United States Patent [19]
Luceri et al.

[11] Patent Number: 4,795,455
[45] Date of Patent: Jan. 3, 1989

[54] SANITARY NAPKIN PAD LINER

[75] Inventors: Thomas J. Luceri, Bridgewater; John Lukjanczuk, Milltown, both of N.J.

[73] Assignee: Personal Products Company, Milltown, N.J.

[21] Appl. No.: 91,248

[22] Filed: Aug. 31, 1987

[51] Int. Cl.[4] .............................................. A61F 13/16
[52] U.S. Cl. ................................................ 604/386
[58] Field of Search ................ 604/385.1, 386, 385, 604/378, 389, 390, 379, 382, 370, 366

[56] References Cited

U.S. PATENT DOCUMENTS 4,059,114  11/1977  Richards .............................. 604/360
4,624,666  11/1986  De Rossett et al. ................. 604/378
4,657,538   4/1987  Becker et al. ...................... 604/378 X Primary Examiner—John D. Yasko

[57] ABSTRACT

A napkin pad liner is provided which is designed to be used with a conventional sanitary napkin to provide more rapid fluid take-up and reduced fluid strikeback. The liner includes a cover of a non-wettable, fluid permeable hydrophobic material which covers a thin layer of absorbent fabric. Pressure sensitive adhesive is located on the napkin-facing side of the absorbent fabric. The adhesive is protected prior to use of the liner by a release strip. In a preferred embodiment the liner is embossed with a central channel to promote rapid longitudinal fluid distribution at the time of fluid take-up.

16 Claims, 3 Drawing Sheets

SANITARY NAPKIN PAD LINER

This invention relates to products for absorbing body fluids and, in particular, to liners for sanitary napkins.

In general, sanitary napkins and other absorbent products have an absorbent core comprising one or more layers of fluid absorbent material such as wood pulp, rayon, gauze, tissue or the like, and in some cases synthetic hydrophilic material such as hydrophilic polyurethane foam may be used. The hydrophilic material is generally provided in the form of a pad, which may have a rectangular or somewhat oval shape. To enhance the sense of comfort for the user, absorbent products also generally employ a cover material or facing which covers the body-facing surface of the hydrophilic material. The cover is generally made of hydrophobic materials so that it will not be stained by or absorb fluids. The purpose of the cover is to structurally contain the loosely packed absorbent material and to protect the body from direct contact with the absorbent pad. To protect the clothing of the user from being stained or wetted by the body fluids absorbed by the hydrophilic material, the pad is generally backed by a body fluid impervious barrier sheet. The absorbent product is positioned on the body with the hydrophilic material facing the body and the fluid impervious barrier facing the clothing of the user. To retain the product in place during use, pressure-sensitive adhesive is conventionally located on the outer surface of the fluid impervious barrier so that the product may be adhered to the undergarment of the user.

An ideal sanitary napkin should exhibit at least two favorable characteristics. One is a fast fluid absorbency rate, or rapid fluid take-up. At the moment when body fluids contact the cover, the design and materials of the napkin should be such that rapid transmission of the fluids through the cover to the underlying pad is promoted. The fluids should be transmitted to the pad remote from the cover and the body area it contacts as quickly as possible.

A second desirable characteristic is low rewettability, or fluid strikeback. Once a sanitary napkin has absorbed body fluids, the materials and construction of the napkin should be such that the fluids remain within the absorbent core, and are not retransmitted back through the cover to contact the body of the user. A napkin with a low rewettability characteristic will remain comfortable during extended periods of use, even after absorbing a significant amount of body fluids.

A third characteristic of varying necessity is the ability of the product to retain a large volume of fluid. The nee of the user for this characteristic may vary from day to day, or even from hour to hour. During times of light flow or between menstrual periods, a user may need only minimal protection, and hence may prefer to use one of the commercially available thin, protective absorbent napkins, such as that described in U.S. Pat. No. 4,518,451. At such times the thin napkin can provide adequate protection against the soiling of undergarments, while affording a high degree of comfort and a very low profile under clothing.

At other times, however, a user may require a bulkier, more substantial napkin which is capable of absorbing significant amounts of fluid. Finally, there can be times when the user's needs may be variable or uncertain. At those times a user may initially employ a thin napkin, but may need to carry one of the bulkier, more substantial napkins in reserve. Such is not always convenient, however. It would be desirable, then, for a user to carry a thinner, more convenient product which may be used to supplement a thin napkin when the need arises.

In accordance with the principles of the present invention, a sanitary napkin pad liner is provided which may be used in conjunction with any other sanitary napkin. A preferred embodiment of the present invention includes a non-wettable, fluid permeable cover of hydrophobic material. The cover is embossed or laminated to a layer of an absorbent nonwoven material. Located on the napkin-facing side of the nonwoven material is a pressure sensitive adhesive which is sufficient to maintain good contact between the nonwoven material and the sanitary napkin to which it is designed to be adhered. The adhesive area is minimized and selectively located so as to present an insubstantial barrier to fluid transmission. A release strip is placed over the adhesive to protect it from contamination and inadvertent adhesion prior to use.

In a most preferred embodiment, the sanitary napkin pad liner of the present invention includes an embossed pattern on the cover surface. Embodiments of the present invention, when used with a conventional sanitary napkin, have been found to significantly increase the absorbency rate while providing a decrease in fluid strikeback as compared with the conventional sanitary napkin alone.

Figure 1:
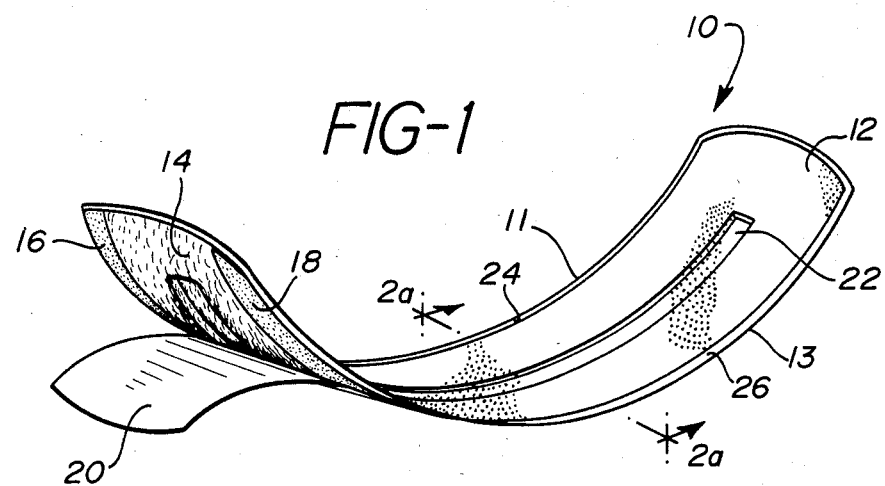
FIG. 1 is a perspective view of a sanitary napkin pad liner constructed in accordance with the principles of the present invention showing both major surfaces of the liner.

Referring to FIG. 1, a sanitary napkin pad liner constructed in accordance with the principles of the present invention is shown. The liner comprises a hydrophilic cover 12 embossed to a high bulk absorbent nonwoven fabric 14. In a preferred embodiment the cover 12 is a coextruded apertured film of two polymeric materials. The outer, body contacting layer comprises essentially linear low density polyethylene, and the inner, fabric contacting layer comprises essentially an ethylene-vinyl acetate (EVA) copolymer. Both layers contain other additives, as described in U.S. patent application Ser. No. 840,290, filed Mar. 14, 1986. A Preferred cover material has an average open area of about 42%, a thickness of about 4.5 mils, and a basis weight of about one oz./yd.$^2$ This cover material is preferred for the ability to achieve heat sealing by melting the inner EVA layer to its melting point, which does not cause the polyethylene layer to melt. The unmelted polyethylene layer thereby maintains the integrity of the film and its apertures during a heat sealing process.

A preferred material for the absorbent nonwoven fabric 14 is a low density, thermally bonded nonwoven fabric comprising a mixture of absorbent fibers, non-wettable polymeric fibers, and conjugate fibers. The absorbent fibers may be wood pulp or other cellulosic fibers which may be treated to enhance absorbency. Suitable conjugate fibers comprise a fiber of a polyester core surrounded by a sheath of polyethylene, and suitable non-wettable polymeric fibers comprise polyester. A highly satisfactory absorbent fabric is provided by a thermally bonded absorbent fabric comprising 44% by weight of wood pulp fibers, 43% by weight of conjugate fibers having a staple length of 3.8 cm and a denier of 3.0, and 13% by weight of polyester fibers having a staple length of approximately 2 in. and a denier of 15. The fabric is stabilized by passing hot air through the fibers and thereby melting the Polyethylene sheaths of the conjugate fibers, which bonds the fabric together upon cooling. Thus it is seen that the conjugate fibers provide integrity for the fabric, the wood pulp provides the desired absorbency, and the polyester fibers maintain the loft of the fabric and its fluid transmitting capillaries between fibers when the wood pulp is saturated with fluid.

Figure 2A:
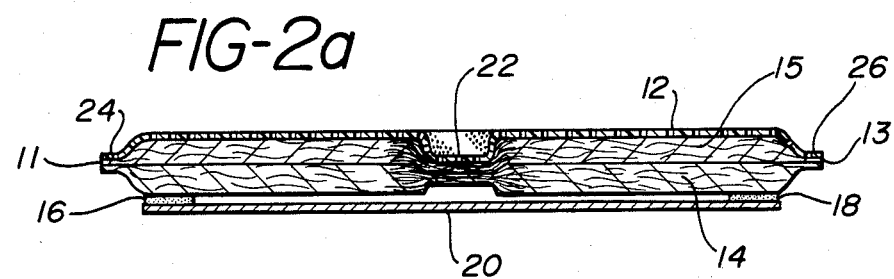
FIG. 2a is a cross-sectional view of a sanitary napkin pad liner constructed in accordance with the principles of the present invention.
Figure 2B:
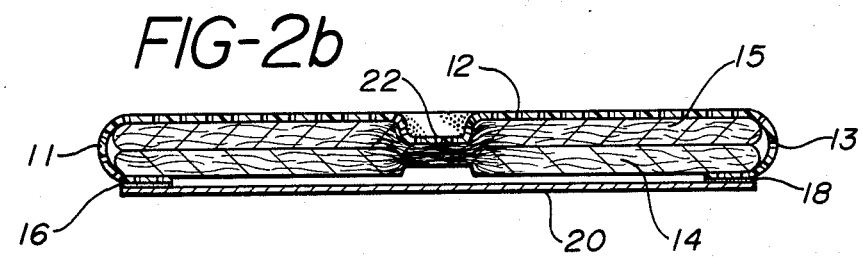
FIG. 2b is a cross-sectional view of the sanitary napkin Pad liner of FIG. 1, taken along lines 2—2 thereof.

Preferably, the layer 14 of absorbent fabric comprises two layers 14 and 15 of a 2.0 oz./yd.$^2$ fabric, as shown in the cross-sectional views of FIGS. 2a and 2b. The two layers are in intimate contact with each other so as to provide a continuous capillary path between the cover 14 and the conventional napkin to which the pad liner is attached. The contact between the two layers and the cover is enhanced and maintained through bonding as described subsequently.

In the embodiment of FIG. 1, the cover material is trimmed flush with the ends of the absorbent fabric 14 at the longitudinal ends of the liner. The cover material at the longitudinal sides 11 and 13 of the liner is folded around the sides of the liner and extends slightly onto the underside of the absorbent fabric. Along the edges of the cover material on the underside of the liner are two lines 16 and 18 of a highly aggressive pressure sensitive adhesive, such as Fuller 6680 hot melt adhesive. These positioning adhesive lines provide a means for attaching the pad liner to a conventional sanitary napkin. The adhesive lines should be narrow (i.e., 0.25 inches or less in width), since they represent a barrier to fluid passing through the pad liner to the underlying sanitary napkin. Preferably the adhesive lines extend in broken or unbroken lines along nearly the entire length of the pad liner, so that intimate contact will be maintained between the absorbent fabric 14 and the face of the underlying sanitary napkin, thereby ensuring good fluid transmissivity.

Covering the adhesive lines is a protective release strip 20 which is provided to protect the adhesive lines from contamination and unintended adhesion prior to use. A particularly useful material is a semibleached kraft paper, the adhesive contacting side of which has been silicone treated to Provide easy release from the adhesive lines 16 and 18.

The napkin pad liner of FIG. 1 is embossed along nearly the entire length of the center of the napkin to form a central channel 22. In a constructed embodiment the central channel 22 had a width of 0.25 inches. The embossed channel not only maintains the integrity of the liner by embossing the cover and absorbent fabric layers together, but it also provides enhanced rapid fluid absorbency and low rewettability characteristics. As compared with other embossing patterns, discussed below, the central channel enhances absorbency by directing rapid deposits of fluid along the channel, from which the fluid is quickly transmitted through the liner. This minimizes fluid build-up at a particular region of the liner and a resultant deposit of fluid in only a limited region of the underlying sanitary napkin. The central channel also minimizes the possibility of fluid transmission laterally to the sides 11, 13 of the liner.

A constructed embodiment of the liner of FIG. 1 measured 1.8 inches wide by 7.6 inches long. These dimensions were chosen so that the liner was sized to correspond with the absorbent face dimensions of most commercially available sanitary napkins.

FIGS. 2a and 2b show cross-sectional views of two napkin pad liners of the present invention. In these FIGURES, the cover and absorbent fabric layers are shown separated for clarity of illustration; i should be understood that the separation of materials does not occur in the embossed liner. In FIG. 2a, the cover 12 and absorbent fabric layers 14 and 15 are all of substantially the same width. The longitudinal edges 11, 13 of the liner are sealed by thermal bonding, as indicated at 24 and 26. The preferred materials readily afford this construction technique, as the EVA layer of the cover 14 melts and bonds to the conjugate fibers of the absorbent fabric. FIG. 2b is a cross-sectional representation of the FIG. 1 embodiment, in which the cover 14 wraps over the longitudinal edges 11 and 13 of the liner. It should also be noted that when the hot melt adhesive lines 16 and 18 are applied along the edges of the cover material, the adhesive will pass through the apertures of the cover 14 and adhere the cover edges to the absorbent fabric 14. Thus, the absorbent fabric is securely enveloped by the cover.

Figure 3A:
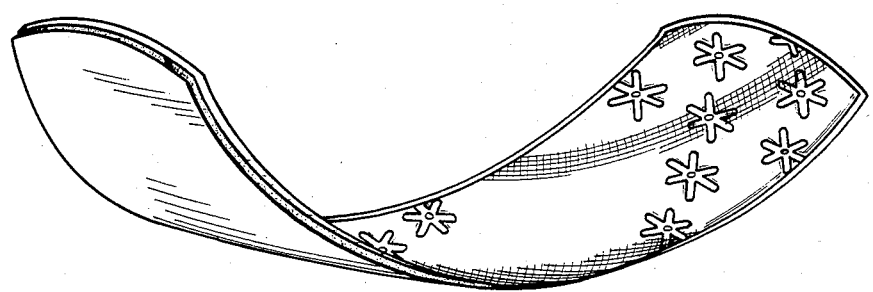
FIGS. 3a–3c illustrate various embossing patterns suitable for use by the liner of the present invention.
Figure 3B:
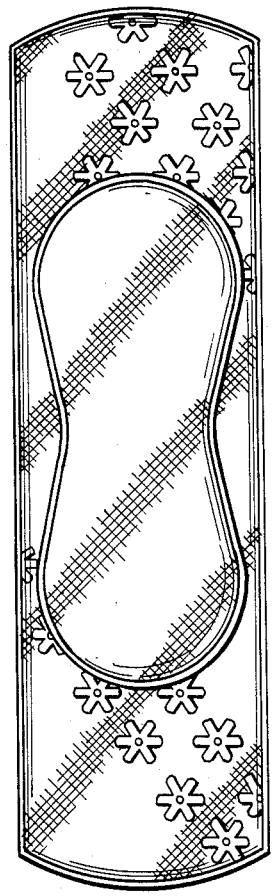
Figure 3C:
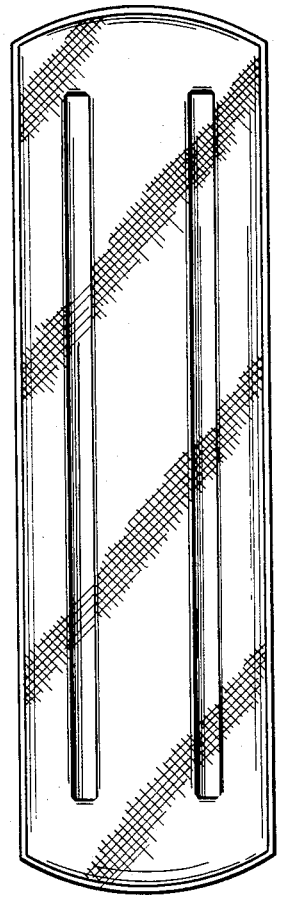

FIGS. 3a, 3b, and 3c illustrate alternative embossing patterns suitable for use in a napkin pad liner of the present invention. FIG. 3a illustrates a liner with an evenly distributed embossed snowflake pattern. The Pattern is embossed in the manner shown in U.S. Pat. No. 4,518,451, with the snowflakes spaced from each other approximately in half-inch spacing. FIG. 3a shows only portions of the embossing; in practice, the pattern covers the entire liner in an even distribution. The snowflake pattern provides depressions in which body fluids may collect for rapid transmission through the liner.

FIG. 3b illustrates an hourglass-shaped embossing, with the area of the liner surrounding the hourglass embossing containing the snowflake embossing. The unembossed area within the hourglass channel maintains a high loft for rapid absorbency of body fluids, unimpeded by thermally compressed and melted areas resulting from embossing. Undesired lateral transmission of body fluids is retarded by the surrounding hourglass channel.

FIG. 3c illustrates the use of two quarter-inch embossed channels entending along opposite sides of the longitudinal center line of the liner.

Embodiments using these three embossing patterns and the central channel of FIG. 1 were all constructed and tested with conventional sanitary napkins for absorption time and rewet capacity. While all embossing patterns were found to enhance these characteristics, particularly absorption time, the greatest improvement was provided by the central channel with its longitudinal fluid distribution property.

The embodiment of FIG. 1 with its central channel was constructed and tested with several commercial sanitary napkins to demonstrate the improved performance provided by tee present invention. Table A shows these test results. The test results are a summary of several individual tests of each napkin or napkin and liner combination. In each case, the napkin pad liner was attached in the manner of its intended use, which is to align the liner with the face of the napkin and secure it to the napkin with the lines of adhesive. The napkin, or the napkin and liner combination, was then saturated by depositing 15 cc of synthetic menstrual fluid on the upward facing cover of the napkin or combination. The time required for the tested item to absorb the fluid was noted and recorded as a 15 cc absorption time. The saturated item was then covered with tissue of a known weight and a plexiglas plate, and a pressure of 0.55 lbs./in.$^2$ was applied to the plate for approximately 3 minutes to induce rewet. The plate was removed and the tissue weighed to determine the amount of fluid which was retransmitted through the cover and absorbed by the tissue. This fluid weight was recorded as the 15 cc rewet amount in grams. The test results of Table A show a significant improvement in fluid absorbency time and in rewet values provided by the combinations of the commercial napkins and the liner ⓒf the present invention as compared with these properties of the commercial napkins alone.

TABLE A

| Product/Combination | 15 cc Absorption Time (sec.) | Rewet 15 cc (grams) |
|---|---|---|
| SURE & NATURAL ® Napkin alone | 17.4 | 3.8 |
| SURE & NATURAL ® Napkin/Liner | 8.6 | 2.3 |
| New Freedom ® Thins napkin alone | 58.1 | 5.2 |
| New Freedom ® Thins napkin/Liner | 11.9 | 2.5 |
| Tampax Maxithins ® Napkin alone | 11.7 | 3.2 |
| Tampax Maxithins ® Napkin/Liner | 7.7 | 0.6 |

The foregoing test results demonstrate that, since the napkin pad liner of the present invention improves the absorbency rate for commercially available sanitary napkins, it is expected that a user will experience a reduced incidence of failure. This is because one mechanism of napkin failure is a rapid deposition of fluid at a rate greater than the rate at which the napkin can absorb the fluid. When this occurs, the fluid can puddle on the napkin surface and flow laterally beyond the sides of the napkin face before it can be absorbed. The napkin pad liner of the present invention improves the rate of absorbency, thereby reducing the instances of failure by this mechanism.

Second, because the napkin pad liner of the present invention reduces rewet, the user should stay drier during use. The napkin pad liner acts to keep a greater amount of the absorbed fluid away from the surface of the liner cover, and away from the user's body. Additionally, the preferred apertured film cover provides a cleaner appearance after the liner is used than does the cover of many commercially available napkins.

Third, a distinct advantage of the napkin pad liner of the present invention is that a user can select when to use it. For instance, the user may elect to use the liner with her normal sanitary napkin during heavy flow days, while dispensing with the liner during light flow days when a rapid absorbency rate may not be required. Furthermore, the thin liner may be conveniently carried by the user in a pocket or purse.

Figure 4:
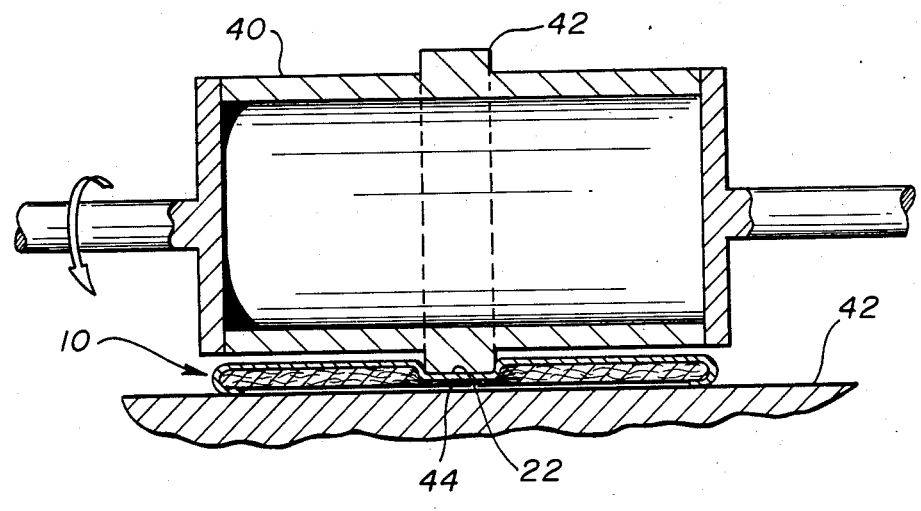
FIG. 4 illustrates a technique for embossing a sanitary napkin pad liner of the present invention with a central channel.

FIG. 4 illustrates a technique for embossing the central channel 22 in the napkin pad liner of FIG. 1. In FIG. 4, an embossing roller 40 is shown in cross-section with a central raised area 42. The embossing roller 40 opposes a smooth anvil roller 42 with a nip 44 therebetween. Positioned between the rollers and within the nip is the napkin pad liner 10. The two rollers are adjustably spring loaded so as to urge them together and close the nip 44. By virtue of the spring loading the two rollers are urged together, and are separated by a distance corresponding to the resistance to compressive forces of the liner materials. In the nip area, the liner is compressed to its limiting value, thereby forming the central channel 22. The embossing process may be conducted using an embossing roller surface temperature in the typical range of 93°-121° C., a set gap between the anvil and embossing rollers of about 0.0025 cm., and an embossing pressure in the nip area in excess of 500 lbs./linear inch.

What is claimed is:

1. A napkin liner for use in conjunction with a sanitary protection product comprising:
   a substantially non-wettable, fluid permeable cover of hydrophobic material located on the body-facing side of the liner;
   a thin layer of absorbent material for transmitting body fluids which have passed through the cover material to an underlying sanitary protection product;
   adhesive means, located on the sanitary protection product facing side of said liner, for attaching said liner to an underlying sanitary protection product, said adhesive means posing a relatively insubstantial barrier to the transmission of body fluids through said liner to an underlying absorbent product; and
   release strip means for covering said adhesive means to prevent inadvertent adhesion of said liner prior to use.

2. The napkin liner of claim 1, wherein said liner is embossed with a pattern.

3. The napkin liner of claim 2, wherein said embossed pattern comprises a central, longitudinal channel.

4. The napkin liner of claim 3, wherein said central, longitudinal channel has a width of approximately one-half inch.

5. The napkin liner of claim 2, wherein said embossed pattern comprises a snowflake-like pattern evenly distributed over the surface of said cover.

6. The napkin liner of claim 2, wherein said embossed pattern comprises an hourglass-shaped channel.

7. The napkin liner of claim 6, wherein the surface of said cover surrounding said hourglass-shaped channel is embossed with a snowflake-like pattern.

8. The napkin liner of claim 2, wherein said embossed pattern comprises two longitudinal channels respectively offset on either side of the longitudinal center line of said liner.

9. The napkin liner of claim 1, wherein said adhesive means comprises two lines of pressure-sensitive adhesive locate along the longitudinal edges of said layer of absorbent material so as to pose a relatively insubstantial barrier to the transmission of body fluids through the center of said liner.

10. The napkin liner of claim 9, wherein said adhesive lines are one-half inch in width or less so as to pose a relatively insubstantial barrier to the transmission of body fluids through the center of said liner.

11. The napkin liner of claims 1, wherein said cover material comprises a thermally bondable material and said thin layer includes thermally bondable fibers,
   wherein said cover is thermally bonded to said thin layer about the periphery of said liner.

12. The napkin liner of claim 11, wherein said thin layer comprises a low density mixture of absorbent fibers and conjugate fibers.

13. The napkin liner of claim 12, wherein said thin layer comprises a thermally bonded nonwoven fabric, and further includes non-wettable polymeric fibers for maintaining the loft of said fabric.

14. The napkin liner of claim 13, wherein said fabric comprises two layers of a 2.0 oz./yd.$^2$ nonwoven.

15. A napkin liner for use in conjunction with a sanitary protection product comprising:
- a substantially non-wettable, fluid permeable cover of hydrophobic material located on the body-facing side of the liner;
- a thin layer of absorbent material for transmitting body fluids which have passed through the cover material to an underlying sanitary protection product;
- adhesive means, located on the sanitary protection product facing side of said liner, for attaching said liner to an underlying sanitary protection product, said adhesive means posing a relatively insubstantial barrier to the transmission of body fluids through said liner to an underlying absorbent product; and release strip means for covering said adhesive means to prevent inadvertent adhesion of said liner prior to use;

wherein the longitudinal edges of said cover material overwrap the longitudinal sides of said liner and the longitudinal edges of the sanitary protection protection product facing side of said layer of absorbent material; and wherein said adhesive means comprises two lines of pressure sensitive adhesive located along the overwrapped longitudinal edges of said cover material on the sanitary protection product facing side of said layer of absorbent material.

16. The napkin liner of claim 15, wherein said adhesive means further comprises means for adhering the overwrapped longitudinal edges of said cover material to the sanity protection product facing side of said layer of absorbent material.

* * * * *